(12) United States Patent
Abraham-Fuchs et al.

(10) Patent No.: US 7,315,784 B2
(45) Date of Patent: Jan. 1, 2008

(54) NETWORK FOR EVALUATING DATA OBTAINED IN A BIOCHIP MEASUREMENT DEVICE

(75) Inventors: Klaus Abraham-Fuchs, Erlangen (DE); Arne Hengerer, Erlangen (DE); Norbert Windhab, Hofheim (DE); Kieran T. Gallahue, San Diego, CA (US); James P. O'Connell, Solana Beach, CA (US); Greg Gosch, Carlsbad, CA (US)

(73) Assignees: Siemens Aktiengesellschaft, Munich (DE); Nanogen, Inc., San Diego, CA (US)

( * ) Notice: Subject to any disclaimer, the term of this patent is extended or adjusted under 35 U.S.C. 154(b) by 1157 days.

(21) Appl. No.: 09/784,720

(22) Filed: Feb. 15, 2001

(65) Prior Publication Data

US 2002/0120183 A1 Aug. 29, 2002

(51) Int. Cl.
- *G06F 19/00* (2006.01)
- *G01N 33/48* (2006.01)
- *A61B 5/00* (2006.01)
- *C12Q 1/00* (2006.01)

(52) U.S. Cl. .................. 702/19; 702/22; 702/189; 600/300; 435/287.1; 435/4

(58) Field of Classification Search .................. 702/19, 702/20
See application file for complete search history.

(56) References Cited

U.S. PATENT DOCUMENTS

| | | | | |
|---|---|---|---|---|
| 4,658,370 | A * | 4/1987 | Erman et al. | 364/513 |
| 5,924,074 | A * | 7/1999 | Evans | 705/3 |
| 6,248,063 | B1 * | 6/2001 | Barnhill et al. | 600/300 |
| 6,267,722 | B1 * | 7/2001 | Anderson et al. | 600/300 |
| 6,454,709 | B1 * | 9/2002 | Kleinschmidt et al. | 600/300 |
| 6,484,104 | B2 * | 11/2002 | Abraham-Fuchs et al. | 702/19 |
| 2004/0018519 | A1 * | 1/2004 | Wright, Jr. | 435/6 |

FOREIGN PATENT DOCUMENTS

| | | |
|---|---|---|
| WO | WO 97/05553 | 2/1997 |
| WO | WO 97/29447 | 8/1997 |
| WO | WO 99/05591 | 2/1999 |
| WO | WO 00/41613 | 7/2000 |
| WO | WO 01/16860 | 3/2001 |

OTHER PUBLICATIONS

Rindfleisch et al. Directions for Clinical Research and Genomic Research inot the Next Decade: Implications for Informatics. Journal of American Medical Informatics Association. Sep./Oct. 1998, vol. 5, No. 5, pp. 404-411.*
Mendoz et al. High-Throughput Microarray-Based Enzyme-Linked Immunosorbent Assay (ELISA). BioTechniques. Oct. 1999, vol. 27, pp. 778-788.*
Merriam-Webster's Collegiate Dictionary Tenth Edition. 1999, p. 1066 (term sensitive and sensitivity).*
Kulikowski et al. Proc. of ACM Conference on History of Medical Informatics. Dec. 1987, pp. 199-206.*
Su, Mu-Chun. Computers in Biology and Medicine. 1994. vol. 24, No. 6, pp. 419-429.*

* cited by examiner

*Primary Examiner*—Marjorie A. Moran
(74) *Attorney, Agent, or Firm*—Schiff Hardin LLP

(57) ABSTRACT

In a method and a network for evaluating medical data in a clinical study, biochips containing patient samples with multiple biomolecular markers are tested in a number of point of care test devices respectively at point of care sites. Each test of each biochip sample produces a diagnostic result, which is entered into the electronic patient record for the patient who produced the sample. A follow-up examination is subsequently conducted for each patient, and the results of the follow-up examination are also entered into that patient's electronic patient record. The follow-up results indicate whether the diagnostic test result was a false positive, a false negative or correct. The follow-up data and the original diagnostic results from all point of care sites are electronically transmitted to a remote server, which has access to an expert system which uses the test results and the follow-up data to automatically devise a measurement protocol for a selected pathology.

16 Claims, 2 Drawing Sheets ent record (EPR) is produced,
NETWORK FOR EVALUATING DATA OBTAINED IN A BIOCHIP MEASUREMENT DEVICE

BACKGROUND OF THE INVENTION

1. Field of the Invention

The present invention is directed to an arrangement for reading and evaluating data from a biosensor array (biochip) for medical diagnostic purposes.

2. Description of the Prior Art

It is well-known that the presence of certain biomolecules, such as a particular protein, antibody or DNA fragment, in the human body is correlated with certain diseases, and therefor it is also known to make a medical diagnosis based on identification of the presence of these biomolecules. If the presence of a certain molecular species at a certain concentration level in the human body has been shown to be correlated with the presence or absence of a particular pathology (disease), the relevant biomolecule is referred to as a diagnostic marker for the pathology. For most diseases, the pathological reaction chain is very complex, and involves a large number of different biomolecules which, in turn, also may play a role in the pathophysiology of another disease. Therefore, a single marker is not always sufficient in order to unequivocally diagnose a particular disease. Often, it is only through an evaluation protocol involving several combined markers that a diagnosis can be made. For example, if a concentration is high for a first marker, low for a second marker, and a third marker is absent, then a particular disease can be diagnosed. The measurement of single markers or multiple markers is referred to as an in vitro diagnostic test. The development of markers for such diagnostic tests is very cost intensive and time intensive, and the development of expert rules for such tests is even more cost intensive and time intensive. The establishment of a marker rule or a multi-marker rule requires a procedure known as a clinical test or clinical study (sometimes merely called a "clinical"). The clinical study includes measuring candidate markers in a large number of patients, usually hundreds to thousands of patients. From such data, a diagnosis standard is established, which will always have a certain error associated therewith. In order to determine whether the error is within an acceptable range, as well as to determine whether refinements or modifications in the standard reduces the error, it is necessary to retrospectively correct results which are "predicted" by the standard with actual follow-up examinations of the patients. The results from such a clinical study are the basis for approval of such a diagnostic test by a national authority, such as the FDA in the United States.

SUMMARY OF THE INVENTION

It is an object of the present invention to provide a cost-efficient and clinically reliable way of obtaining clinical measurement and diagnosis data for a new diagnostic marker or a new multi-marker expert rule, which is suitable for collecting a volume of data sufficient to support an approval procedure for the marker or rule with a national health authority, such as the FDA.

The above object is achieved in accordance with the principles of the present invention in a network and a method for collecting data and diagnostic testing wherein a biochip with a multi-marker diagnostic test is employed. The biochip has a marker array, which can include "hidden" markers in addition to approved markers, the "hidden" markers not being used for making a current diagnostic decision with the approved markers. For each investigated patient, and electronic patient record (EPR) is produced, wherein the measurement results from the biochip are stored, including the "hidden" markers, if present. The final target diagnostic decision obtained from the measurement results is also stored in the EPR. These entries into the patient's EPR can be stored in the same data file on the same storage device as the measurement results from the biochip, or can be organized as separate segments of a physically distributed EPR, the different segments being connected by means of a digital data network. A central data bank is in communication with storage sites for the individual EPRs of the patients enrolled in a clinical study, and the central data bank collects the data from all of the individual EPRs. Follow-up data are entered into the EPRs, which indicates whether the diagnosis based on the biochip measurement was, in fact, correct. The central data bank is in communication with a processor which employs an algorithm to test new hypotheses on the data stored in, or accessible by, the central data bank, so as to identify optimized evaluation rules for new or existing multi-marker tests. The evaluation rules are presented at a user interface, and may be documented together with the underlying EPR clinical study data for an approval procedure. The data link between the central data bank, which can be a central server, and the individual storage sites for the EPRs (or sites for EPR data entry) can be conducted via the Internet or e-mail.

For collecting the data, a disposable biochip with a patient sample can be obtained in a known manner for each patient. The disposable chip with the patient sample is then inserted into a suitable measurement device, wherein the measurement or measurements are conducted in a known manner. The results of the measurement can be displayed at the point of care test device, and/or can be stored at the test device site, but this is not essential. The raw point of care data (POC data) are then sent to a data evaluation site at a remote server. The data evaluation at the remote server can take place using an expert system operating according to expert rules, such as a neural network. An evaluation result (diagnosis) is thus obtained, and is transmitted back to the point of care site. This evaluation result is then displayed at the point of care site.

By collecting and combining the data and diagnosis results from a large number of point of care sites in communication with the remote server, a large data bank can be accumulated, with which the expert rules employed in the data evaluation can be refined and/or modified by a suitable learning procedure in the expert system.

DESCRIPTION OF THE PREFERRED EMBODIMENTS

The present invention makes use of currently available biosensor arrays (biochips) and Electronic Patient Records (EPR).

A new generation of biosensor arrays has been developed and is about to enter widespread use in the medical diagnostic market. Instead of conducting multiple measurements of multiple markers with a number of different devices, or using highly sophisticated robots in a centralized diagnostic laboratory, the new generation of biosensor arrays are able to measure, in a fully automated manner, a large number of markers simultaneously, up to thousands of different markers on the same chip, without a need for further human interaction. Moreover, such measurement are made outside of a formal laboratory environment. Almost all known types of biomolecular markers (e.g. DNA fragments, proteins, enzymes, antibodies, etc.) can be measured simultaneously on the same chip. These biochips are particularly suited for immediately conducting the diagnostic test at a point of care (POC) site, such as a hospital bedside, a physician's office, or even at the patient's home. Such biochips also, of course, can be used in a professional centralized laboratory.

A well documented trend in healthcare systems is the increasing establishment and use of electronic patient records, i.e., electronic media wherein all medically relevant information for a particular patient are stored. Such information can include, for example, diagnoses, measurement results, x-ray images or other medical images, records of therapeutic actions taken, surgical interventions, vaccinations, prescribed medications, etc. The data can be stored at distributed locations, usually at the site where the data or information was created or entered. With increasing access to the Internet, there is a known trend to connect such distributed sites for EPRs via a central server, which regulates access rights to the data relating to respective patients.

The present invention makes use of such biosensor arrays and EPRs to allow data to be collected, and to allow expert rules to be optimized, in the context of a clinical study with the goal of obtaining regulatory approval, such as through the FDA.

Figure 1:
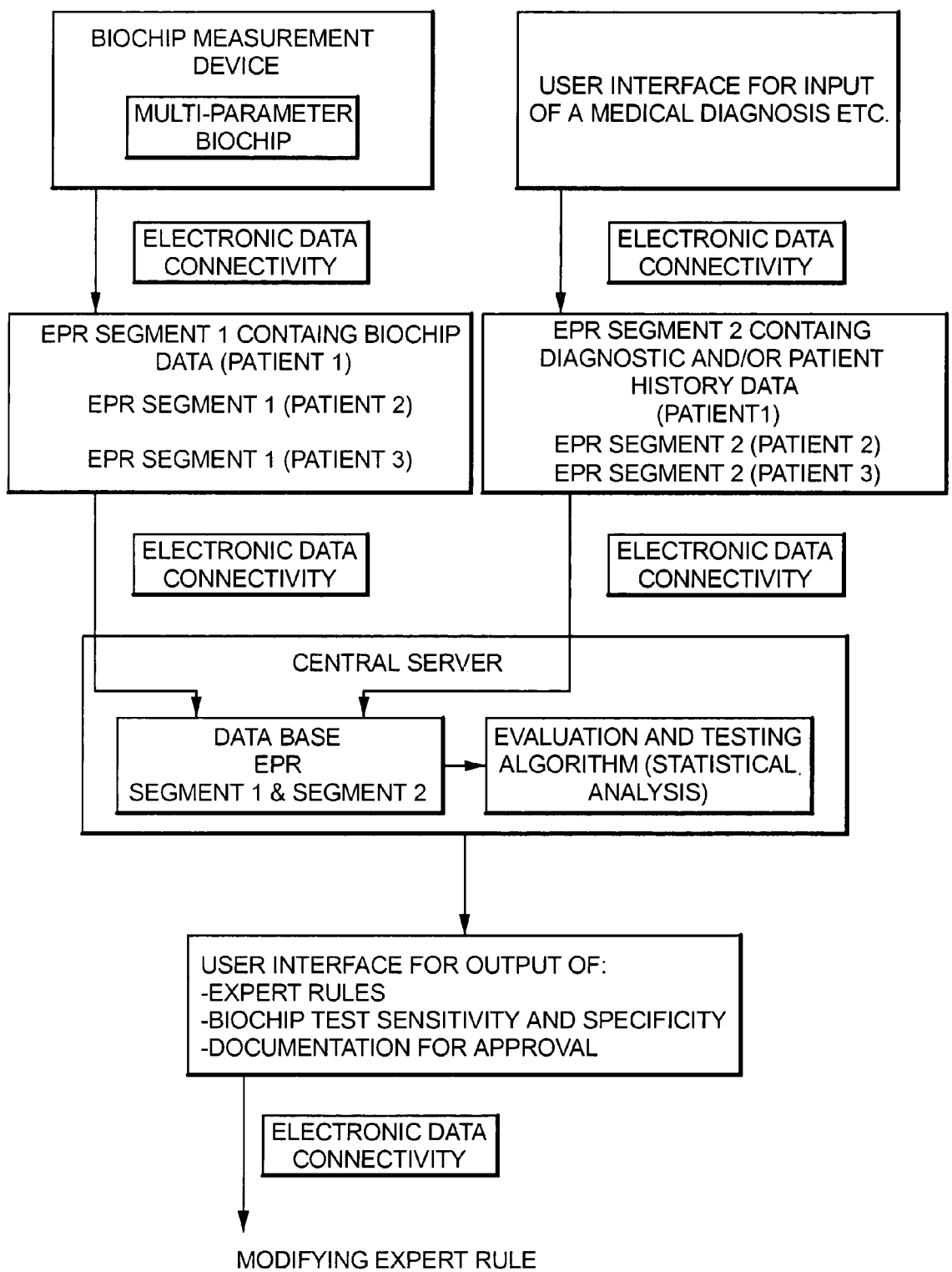
FIG. 1 shows the basic steps and components in the method and network of the invention.

As shown in FIG. 1, the inventive apparatus includes a biochip measurement device, for use with a number of multi-parameter biochips. By means of known measurements in the biochip measurement device an EPR segment 1 containing biochip data is produced for each of a number of patients (patient 1, patient 2, patient 3, etc.).

The apparatus also includes a user interface for entering medical diagnostic data, collectively referred to herein as clinical data, which includes diagnostic data and/or patient history data. Through an electronic connection, the user interface produces, for each patient, an EPR segment 2 containing the diagnostic and/or patient history data.

The EPR segments 1 and the EPR segments 2 are electronically transmitted to a database in a central server, wherein they are stored. The central server also includes a unit for evaluation and testing of the information in the database, according to algorithms for performing statistical analysis. The central server is connected to a user interface, at which expert rules, such as for a measurement protocol for a selected pathology, are displayed as a result of the evaluation and testing conducted in the central server. The user interface also makes available information regarding biochip test sensitivity and specificity, and if necessary, documentation for approval of the measurement protocol.

Through another electronic connection, the expert rule can be modified.

Figure 2:
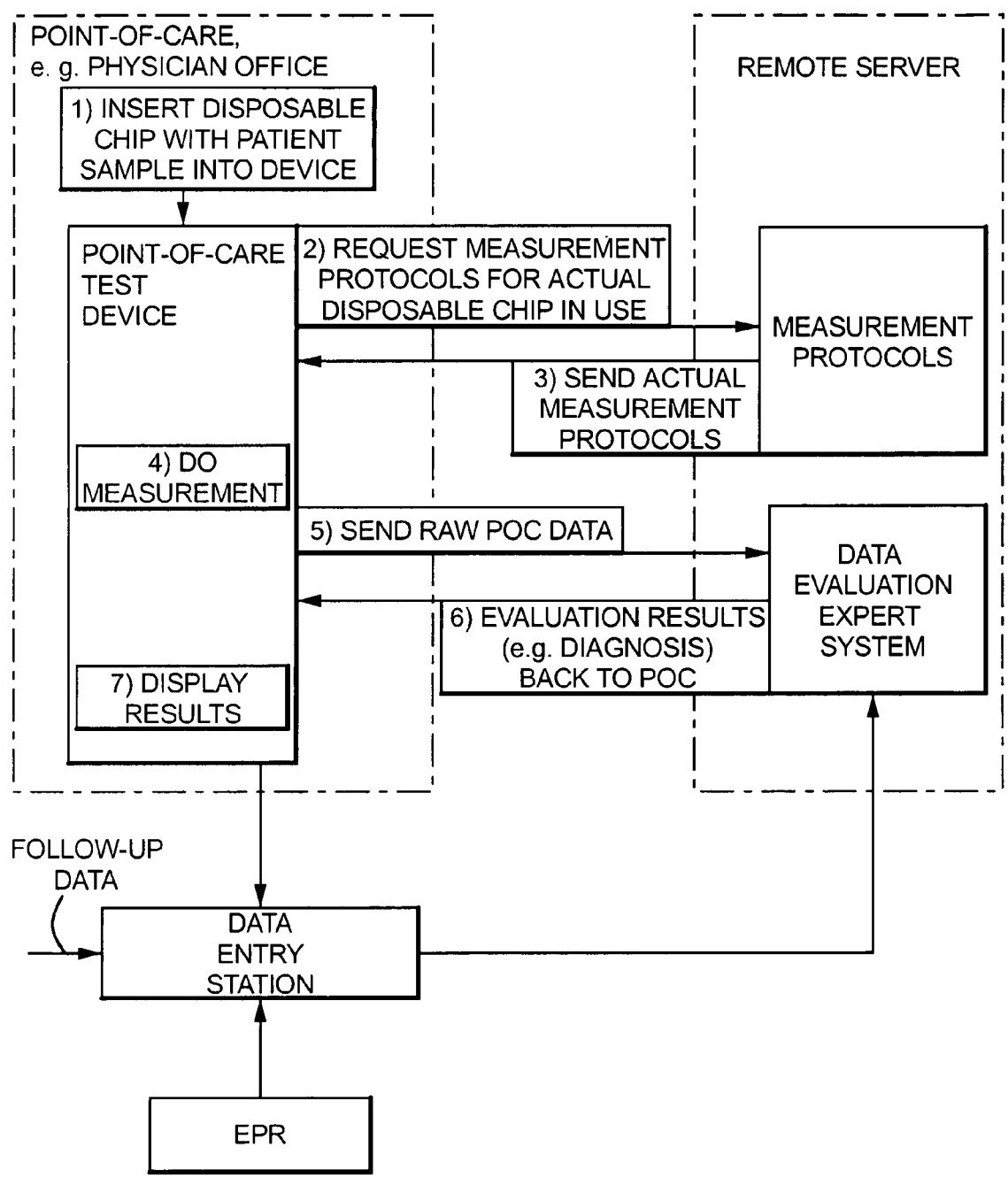
FIG. 2 is a flowchart of an exemplary information exchange procedure in accordance with the invention.

FIG. 2 shows an example of an information exchanges for explaining the manner by which such biosensor arrays and EPRs are used in the inventive network and procedure, assume that a diagnostic test for a certain disease, such as cervical cancer, using five different biomolecular markers, is approved and is regularly practiced in the daily routine in a physician's office to diagnose women with the suspicion of developing this type of cancer, or a screening tool for women who may be at risk from a certain age to develop cervical cancer. A "cervical cancer biochip" is then available for conducting all of the diagnostic tests which are a part of the approved routine for the five markers. For each patient, a disposable biochip with an appropriate sample from the patient is obtained, and the disposable chip with the patient sample is inserted into a suitable point of care test device, such as at the physician's office (step 1 in FIG. 2). The diagnostic test is conducted, possibly with the point of care test device requesting measurement protocols for conducting the tests via a communication link with a remote server (step 2 in FIG. 2). If such a request is made, the remote server, from a data bank of measurement protocols, selects the appropriate measurement protocol and transmits it back via the data link to the point of care test device (step 3 in FIG. 2). Of course, if the protocol is conducted often enough at the point of care test device, the protocol can be stored in the device itself, in which case there is no need to establish communication at the time of the test with the remote server. As used herein a "protocol" not only specifies a procedure, but also the markers which are to be considered in the procedure.

The results of the diagnostic test conducted using the "cervical cancer biochip" are entered into and stored in the EPR of the patient, which is accessible at the point of care site via a data entry station. Since no medical diagnostic test can be unequivocally stated to have a 100% accuracy, there will always be the possibility of a false positive result or a false negative result. In false positive cases, the patient (as a result of the false positive diagnosis) will be referred to a clinic for further evaluation, such as for conducting a biopsy. The biopsy analysis will show that there is, in fact, no cancer present, and this will also be indicated in the patient's EPR. In false negative cases, i.e., where an existing cancer is not diagnosed by the biochip, there will come a time within weeks or months wherein the patient will, in fact, be diagnosed to have cervical cancer, and such a diagnostic entry will be made in the patient's EPR. Thus, over time, every EPR will contain a data entry such as "biochip measurement result" and a follow-up entry (in some form) "cervical cancel diagnosis: positive or negative". Every EPR, therefore, will contain an indication of the correctness of the biochip measurement result which, in turn, is an indication of the efficacy of the protocol used to analyze the biochip data. Automated evaluation of the EPR information is thus able to yield quantified outcome data for the specificity and sensitivity of the "cervical cancer biochip" test under consideration.

As almost always occurs, however, assume that medical progress results in new and possibly more sensitive or more specific markers being identified for cervical cancer. These new markers can be implemented in the context of existing, approved biochip test, as an augmentation in addition to testing for the established markers, and measurement results can be simultaneously obtained. Including these additional markers in the sample and implementing the augmented testing on the markers add virtually no increased cost. The new data are not included in making the diagnostic decision according to the approved protocol, but nevertheless are still stored in the EPR. Since the data are measured and are available together with the final diagnostic result, any hypothesis as to improvement of the sensitivity or specificity can be retrospectively tested, in the same manner described above for the approved protocol. The hypothesis may be, for example, that the additional markers increase performance, or that one marker can replace a less indicative approved marker in the test. The data will establish the basis for final approval of an improved test by a regulatory authority. By such a procedure, a continuous improvement in multi-marker tests is achieved, at virtually no additional cost, using clinical procedures which are already being conducted in any event for the approved procedure. Improved diagnostic markers can thus be developed in a very cost-effective manner.

This is indicated in FIG. 2 in step 4, wherein the measurement is conducted at the point of care testing device using the approved markers as well as the aforementioned "hidden" markers. The raw point of care data obtained as a result of this measurement are transmitted to the remote server, particularly to a data evaluation expert system at, or accessible by, the remote server. The expert system applies expert rules to obtain an evaluation result (diagnosis) in step 6, with this diagnosis result being transmitted back to the point of care site. The diagnosis result can be displayed, in step 7, at the point of care device. The displayed result, however, will be only at this time for the approved test, but the expert system at the remote server can use the totality of the data (i.e., data relating to approved markers as well as "hidden" markers) to execute an appropriate learning procedure so as to adjust or modify the evaluation rules.

Extending this scenario, even diagnostic tests for new diseases can be developed very cost-effectively. For example, assume there exists no currently approved tests for ovarian cancer, but several markers which are indicative of this disease are suggested. Measurement of these markers can be done in the same sample as is used in the "cervical cancer biochip", i.e., a cervical swab. The proposed set of markers for ovarian cancer then can be employed as the "hidden" markers on the chip, and data relating thereto can be measured and stored automatically in the "background" of each cervical cancer test. If any of the women develops ovarian cancer, this will be diagnosed at a later time, and this diagnosis will be entered into the patient's EPR, and retrospectively correlated with the "hidden" biochip test. By collecting such data over a large number of patients, final regulatory approval for an ovarian cancer test can thus be obtained.

The automated, retrospective correlation of biochip measurement data and medical diagnosis in the EPR can also serve to gradually and automatically improve the expert rule for evaluation of a multi-parameter biochip test. An expert rule developed with available data from 500 patients may be improved if optimized based on data from 1,000 patients or 10,000 patients. A browser can automatically evaluate the increasing data base in the various EPRs from an increasing number of patients over predetermined time intervals, such as by using self-learning algorithms in the manner of a neural network to improve the evaluation rules.

Handling of this evaluation procedure is preferably undertaken via electronic data exchange, such as via the Internet or by e-mail, with a central server. The central server automatically collects or receives the necessary data entries from a data bank of EPRs, and then evaluates the sensitivity and specificity of each new multi-parameter test. By centralizing this evaluation procedure, any new hypothesis with respect to the expert rules for biochip evaluation can be rapidly and flexibly tested. Such testing can be undertaken using stored ("old") data from EPRs, or EPRs which are continuously updated, and increasing in number, can be used.

Of course, all of the usual patient and physician agreements must be undertaken to allow a patient to be enrolled in such a clinical study and to allow use of a patient's EPR data in this manner, as well as to allow electronic data transmission of the patient's EPR data.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for analyzing medical data comprising the steps of:
    obtaining a plurality of samples respectively from a plurality of patients and storing the samples respectively in a plurality of disposable biochips, each biochip being sensitive for multiple biomolecular markers;
    providing a plurality of point of care test devices respectively at a plurality of point of care sites;
    respectively receiving said biochips in said point of care test devices, each as a tested biochip, and in each point of care test device performing diagnostic testing on the sample in the tested biochip to obtain raw point of care data;
    entering the raw point of care data as an input to an expert system and producing a diagnostic result with said expert system using an expert rule that identifies a medical condition of the patient from a known correlation of at least one of said multiple biomolecular markers with said medical condition;
    providing a remote server at a location remote from said point of care sites;
    supplying the raw point of care data and an identification of said expert rule from all of the point of care sites, and the follow-up diagnostic data, to said remote server; and
    at said remote server, using all of said point of care data and all of said follow-up diagnostic data as a training data set to identify a previously unknown correlation of at least one further biomolecular marker, among said multiple biomolecular markers, other than said at least one of said multiple biomolecular markers having said known correlation with said medical condition, with a different medical condition represented in said follow-up diagnostic data.

2. The method as claimed in claim 1 comprising using said previously unknown correlation to devise a measurement protocol.

3. The method as claimed in claim 2 comprising using said previously unknown correlation to devise a measurement protocol for a selected pathology.

4. The method as claimed in claim 3 comprising using said previously unknown correlation to automatically devise said measurement protocol.

5. The method as claimed in claim 1 further comprising storing a plurality of measurement protocols in a memory accessible from said remote server, and wherein the step of performing diagnostic testing in each point of care test device comprises establishing a data communication between a point of care test device and said memory to obtain a selected measurement protocol from said memory for use in said point of care test device for performing said diagnostic testing.

6. The method as claimed in claim 5 wherein each of said measurement protocols employs a predetermined number of said biomolecular markers.

7. The method as claimed in claim 6 comprising providing more biomolecular markers in each sample than said predetermined number and wherein the step of performing diagnostic testing includes performing diagnostic testing using said selected measurement protocol and also employing additional biomolecular markers in the sample of the tested biochip, beyond said predetermined number, to obtain augmented testing data, and including said augmented testing data in said raw point of care data.

8. The method as claimed in claim 1 comprising obtaining said follow-up data by conducting a follow-up examination of the tested patient to determine follow-up data indicating whether said test result was a false positive, a false negative or correct.

9. A network for analyzing medical data comprising:
a plurality of disposable biochips, each sensitive for multiple biomolecular markers, respectively for a plurality of patients, each biochip containing a patient sample with multiple biomolecular markers;
a plurality of point of care test devices respectively at a plurality of point of care sites, each point of care test device having an interface in which at least one of said biochips is inserted, as a tested biochip, and having a measurement unit that performs diagnostic testing on the multiple biomolecular markers of the sample in said tested biochip to obtain raw point of care data;
an expert system to which said raw point of care data is entered, as an input, that produces a diagnostic result from said expert system using an expert rule that identifies a medical condition of the patient from a known correlation of at least one of said multiple biomolecular markers with said medical condition;
a plurality of electronic patient records respectively for said patients;
a plurality of point of care data entry stations respectively having access to at least one of said electronic patient records and respectively in communication with said point of care test devices, each data entry station including means for entering follow-up diagnostic data into the electronic patient record for the patient, as a tested patient, who provided the test sample in the tested biochip;
a remote server and an evaluation system accessible by said remote server;
said remote server having at least one data link to each point of care test device and each electronic patient record, for transmitting said point of care raw data of said patient and an identification of said expert rule used to produce said diagnostic result, and said follow-up diagnostic data, to said remote server; and said evaluation system comprising a computer that uses all of said point of care raw data and all of said follow-up diagnostic data as a training data set that identifies a previously unknown correlation of at least one further biomolecular marker, among said multiple biomolecular markers, other than said at least one of said multiple biomolecular markers having said known correlation with said medical condition, with a different medical condition represented in said follow-up diagnostic data.

10. The network as claimed in claim 9 further comprising a memory containing a plurality of measurement protocols accessible by said remote server, and wherein each point of care test device has access to said memory, via said data link, to obtain a selected measurement protocol for performing said diagnostic testing.

11. The network as claimed in claim 9 wherein said expert system is programmed and trained to use said previously unknown correlation to devise a measurement protocol.

12. The network as claimed in claim 11 wherein said expert system is programmed and trained to use said measurement protocol for a selected pathology.

13. The network as claimed in claim 11 wherein said expert system is programmed and trained to automatically devise said measurement protocol.

14. The network as claimed in claim 11 wherein said expert system is programmed and trained to devise said measurement protocol for a specific pathology by testing a predetermined number of said biomolecular markers.

15. The network as claimed in claim 14 wherein said biochips are sensitive for more biomolecular markers than said predetermined number of biomolecular markers, and wherein the measurement protocol operates the respective measurement unit of each point of care test device to execute said diagnostic testing on the biomolecular markers in the sample of the tested biochip to obtain augmented testing data in said raw point of care data.

16. The network as claimed in claim 15 wherein said point of care date entry stations comprise means for entering patient history data into said electronic patient record characterizing whether said diagnostic result was a false positive, a false negative or correct.

* * * * *